United States Patent [19]
Chiarino et al.

[11] Patent Number: 4,632,940
[45] Date of Patent: Dec. 30, 1986

[54] N-SUBSTITUTED 1-(4'-ALKYLSULFONYLPHENYL)-2-AMINO-1,3-PROPANEDIOLS, PHARMACEUTICAL COMPOSITIONS CONTAINING THEM, HAVING LOCAL ANESTHETIC ACTIVITY

[75] Inventors: Dario Chiarino, Monza; Angelo Carenzi, Busto Arsizio; Davide Della Bella, Milan; Mario Fantucci, Piazza Brembana, all of Italy

[73] Assignee: Zambon S.p.A., Vicenza, Italy

[21] Appl. No.: 637,575

[22] Filed: Aug. 3, 1984

[30] Foreign Application Priority Data

Aug. 5, 1983 [IT] Italy ................ 22448 A/83

[51] Int. Cl.$^4$ ................ A61K 31/135; A61K 31/495; C07D 241/04
[52] U.S. Cl. ................ 514/648; 514/649; 514/653; 544/396; 544/398; 544/401; 544/402; 564/316; 564/360
[58] Field of Search ............... 544/402, 396, 398, 401; 514/255, 648, 653, 649; 564/360, 316

[56] References Cited

U.S. PATENT DOCUMENTS

| | | | |
|---|---|---|---|
| 2,759,972 | 8/1956 | Suter | 564/212 |
| 3,056,799 | 10/1962 | Tullar | 260/319 |
| 3,954,871 | 5/1976 | Roba | 564/363 |
| 4,226,808 | 10/1980 | Nagabhushan | 564/212 |

FOREIGN PATENT DOCUMENTS 149750 8/1973 Czechoslovakia .
4987638 8/1974 Japan .

OTHER PUBLICATIONS

Burger, Medicinal Chemistry, 2nd edition, 1960, p. 458.
Benjamin F. Tullar, Chem. Abst. vol. 58, 576d.
Portelli et al, Chem. Abst. vol. 97, 1982, 5886f.
Nagabhushan et al, Chem. Abst. vol. 94, 1981, 46988x.
Diana et al, Chem. Abst. vol. 70, 1969, 11252e.
Budai et al, Chem. Abst. vol. 77, 1972, 5165g.
Kvita et al, Chem. Abst. vol. 80, 1974, 59684f.
Budai et al, Chem. Abst. vol. 77, 1972, 88069c.

*Primary Examiner*—Donald G. Daus
*Assistant Examiner*—Cecilia Shen
*Attorney, Agent, or Firm*—Cushman, Darby & Cushman

[57] ABSTRACT

N-substituted derivatives of 1-(4'-alkylsulfonylphenyl)-2-amino-1,3-propanediol, their salts with pharmaceutically acceptable organic and inorganic acids, processes for preparing them, pharmaceutical compositions containing them and intermediates useful in the preparation thereof.

The novel derivatives according to this invention are endowed with local anesthetic activity.

8 Claims, No Drawings

N-SUBSTITUTED 1-(4'-ALKYLSULFONYLPHENYL)-2-AMINO-1,3-PROPANEDIOLS, PHARMACEUTICAL COMPOSITIONS CONTAINING THEM, HAVING LOCAL ANESTHETIC ACTIVITY

DESCRIPTION

This invention relates to novel N-substituted derivatives of 1-(4'-alkylsulfonylphenyl)-2-amino-1,3-propanediol, to their salts with pharmaceutically acceptable organic and inorganic acids, to the processes for preparing them, to the pharmaceutical compositions containing them and to intermediates useful in the preparation thereof.

More particularly this invention relates to the compounds of Formula:

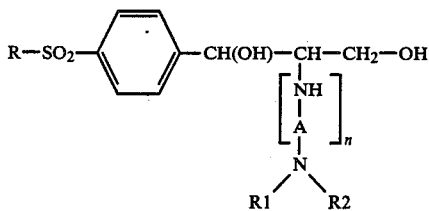

(I)

wherein
R is an alkyl radical having from 1 to 4 carbon atoms;
n is 0 or 1;
A is an alkyl radical having from 2 to 6 carbon atoms;
R1 is hydrogen or an alkyl radical having from 1 to 6 carbon atoms;
R2 is an alkyl radical having from 1 to 6 carbon atoms, a phenoxyalkyl radical, a mono- or di-phenylalkyl radical where the alkyl radical has from 1 to 6 carbon atoms and the phenyl moiety can be substituted by one or two substituents, equal or different between them, which are selected from the group comprising halogen, 1–4C alkyl and 1–4C alkoxy, or
R1 and R2, together with the nitrogen atom to which they are linked, form a 5–6 membered heterocyclic ring which can contain another hetero-atom selected from the group comprising oxygen, sulfur, nitrogen and nitrogen substituted by a 3–6C cycloalkyl, a 1–6C alkyl or by a mono- or a diphenylalkyl radical where, in turn, the alkyl radical has from 1 to 6 carbon atoms and the phenyl moiety can be substituted by one or two substituents, equal or different between them, which are selected from the group comprising halogen, 1–4C alkyl and 1–4C alkoxy, and their salts with pharmaceutically acceptable organic or inorganic acids.

The compounds (I) can exist in various stereoisomeric forms in that they contain two asymmetric carbon atoms and other asymmetric carbon atoms may be present in R1 and R2. This invention relates either each stereoisomer or the mixtures thereof.

As to the meanings of A, R, R1 and R2, the term "alkyl" is intended to comprise either straight or branched chains as well as saturated and unsaturated chains.

Preferred meanings are:
R=methyl or ethyl;
n=0 or 1;
A=ethyl;
R1=hydrogen, methyl or ethyl;
R2=alkyl radical having from 1 to 4 carbon atoms, phenoxyalkyl radical, mono- and diphenylalkyl radical where the alkyl radical has from 1 to 6C atoms and the phenyl moiety can be substituted by one or two substituents, equal or different between them, which are selected from the group comprising halogen and 1–4C alkoxy,
R1 and R2, together with the nitrogen atom to which they are linked, form a piperazinyl radical where the terminal nitrogen is substituted by a cyclohexyl, a diphenylmethyl or a di(fluorophenyl)methyl radical.

The compounds (I) according to this invention can be prepared according to various methods.

The preferred method is consisting in reacting a propanediol of Formula I wherein n is 0 and R1=R2=H, with a suitable carbonyl derivative to afford an acylamino derivative or a Schiff base and in their subsequent reduction to give the compounds I wherein R1=H.

Some intermediates which are thus obtained are novel and are a further object of this invention.

More particularly, the compounds of Formula

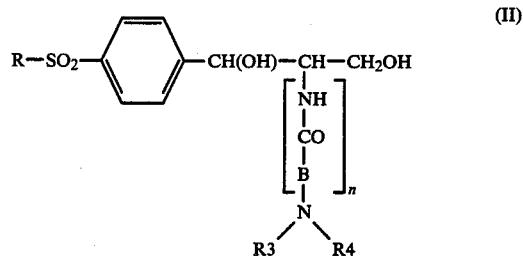

(II)

wherein
R is an alkyl radical having from 1 to 4 carbon atoms.
B is an alkyl radical having from 1 to 5 carbon atoms, and
when
n is 0
R3 is hydrogen,
R4 is a phenyloxyalkanoyl, a mono or a di-diphenylalkanoyl radical, where the alkanoyl radical has from 1 to 6 carbon atoms and the phenyl moiety can be substituted by one or two substituents, equal or different between them, which are selected from the group comprising halogen, 1–4C alkyl and 1–4C alkoxy, or
R3 and R4, together, are phenoxyalkylidene, mono- or di-phenylalkylidene, where the alkylidene radical has from 1 to 6 carbon atoms and the phenyl moiety can be substituted by one or two substituents, equal or different between them, which are selected from the group comprising halogen, 1–4C alkyl or 1–4C alkoxy,
and when n is 1,
R3 is an alkyl having from 1 to 6 carbon atoms,
R4 is an alkyl having from 1 to 6 carbon atoms, or
R3 and R4, together with the nitrogen atom to which they are linked, form a 5–6 membered heterocyclic ring which can contain another hetero-atom selected from the group comprising oxygen, sulfur, nitrogen and nitrogen substituted by a 3–6C cycloalkyl, a 1–6C alkyl or by a mono- or a diphenylalkyl radical where, in turn, the alkyl radical has from 1 to 6 carbon atoms and the phenyl moiety can be substituted by one or two substituents, equal or different between them, which are selected from the group comprising halogen, 1-4C alkyl and 1-4C alkoxy.

Suitable carbonyl derivatives which can be reacted with the compounds of Formula I where R1=R2=H are the aldehydes, the ketones or the acyl halides, esters and anhydrides.

When the carbonyl derivative is an acyl halide, the reaction is preferably carried out according to known techniques in the presence of a suitable diluent and of an organic or inorganic base to capture the hydrogen halide formed during the reaction.

When the carbonyl derivative is an aldehyde or a ketone the reaction is preferably carried out according to known techniques by using an apparatus which allows to separate the water formed during the reaction. An example of such an apparatus is the Dean and Stark separator.

Also the subsequent reduction of the acylamino derivative or of the Schiff base is carried out according to known techniques. In case of acylamino derivatives the preferred reducing agent is lithium aluminium hydride.

In case of Schiff bases the preferred reducing agents are lithium aluminium hydride and sodium borohydride.

The thus obtained compound of Formula I where R is hydrogen can be, if desired, again alkylated. Also this reaction is carried out according to known techniques such as the Leuckart-Wallach reaction.

Another method particularly useful for preparing the compounds of Formula I where R1 and R2 form a heterocyclic ring is consisting in reacting a compound of Formula I wherein both R1 and R2 are hydrogen with a compound of formula X—(CH$_2$)$_n$—Y—(CH$_2$)$_m$—X wherein n is 1, 2 or 3, m is 1, 2 or 3, provided that m+n is 3 or 4, X is halogen, mesyloxy or tosyloxy, Y is O, S, NH or a tertiary nitrogen. Also this reaction is carried out by capturing the hydrogen halide which is formed according to known techniques such as, for example, the addition of suitable organic or inorganic bases.

Alternatively, the above mentioned techniques can be applied to a precursor which can then be easily transformed into the desired compound of Formula I.

Examples of useful precursors are the aminoketones of Formula

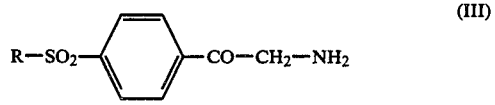

wherein R has the above mentioned meanings, which can firstly be acylated and then treated with formaldehyde to give a 1-(p-alkylsulphonylphenyl)-2-acylamino-1,3-propanediol which is finally reduced to the corresponding compound of Formula I.

The reduction of the keto group to alcohol and that of the acylamino group or of the Schiff base can proceed contemporaneously or in the desired sequence.

Other suitable precursors are the methylthio-analogs of the Compounds of Formula I which can be easily oxydized according to known techniques to afford the Compounds of Formula I;

In view of the desired final compound as well as of the cost and of the availability of the raw materials, the artisan will be able to choose case by case other strategies of synthesis which make use of known techniques.

The novel Compounds of Formula I are endowed with local anesthetic activity.

The evaluation of the local anesthetic activity has been performed with the test of the intradermal infiltration in the back of guinea-pig according to E. Bulbring and I. Wayda (J. Pharmacol. 85, 78–84, 1945).

The local anesthetic activity has been referred as drug concentration (mM) inhibiting the 50% of the occurence of the cutaneous reflex after stimulation (Table 2).

The relationship between the chemical structure of various compounds and their code numbers is shown in Table 1.

Toxicity study in mouse has been performed by intravenous administration. The Compounds have been administered as hydrochloride. After treatment the animals have been observed for 24 hrs.

TABLE 1

RELATIONSHIP BETWEEN CHEMICAL STRUCTURE AND CODE NUMBER

| CODE NUMBER | R | R1 | n | R2 | CONFIGURATION | SALT |
|---|---|---|---|---|---|---|
| Z 1396 | CH | H | 0 | —CH$_2$—CH$_2$—CH(C$_6$H$_5$)$_2$ | 1S, 2S | acid maleate |
| Z 1395 | CH | H | 0 | " | 1R, 2S | " |
| Z 1420 | CH | H | 0 | —CH(CH$_3$)—CH$_2$—CH$_2$—C$_6$H$_5$ | 1S, 2S 1'S* | hydrochloride |
| Z 1421 | CH | H | 0 | " | 1R, 2R, 1'R | " |
| Z 1422 | CH | H | 0 | —CH$_2$—CH(CH$_3$)—C$_6$H$_5$ | 1S, 2S, 2'R* | " |
| Z 1402 | CH | H | 0 | —CH(CH$_3$)—CH$_2$—O—C$_6$H$_5$ | 1S, 2S, 1'S* | — |
| Z 1403 | CH | H | 0 | " | 1S, 2S, 1'R* | — |
| Z 1441 | CH | CH | 0 | " | 1R, 2R, 1'R* | — |
| Z 1442 | CH | H | 0 | " | 1R, 2R 1'S* | — |

The asterisk has been used to distinguish one diastereoisomer from the other as follows:
R, R, R* and S, S, S* are used in connection with the diastereoisomer having the highest retention time in TLC (eluent: dichloromethane/methyl alcohol/ammonium hydroxide).

TABLE 2

| | Local anesthetic activity (local infiltration in the back of guinea pig) |
|---|---|
| COMPOUND | LOCAL ANESTHETIC ACTIVITY ED$_{50}$ (c.l. 95%) (mM) |
| Z. 1402 | 0.075 (0.05–0.1) |
| Z. 1403 | 0.049 0.072) |
| Z. 1396 | 0.36 (0.21–0.60) |
| Z. 1395 | 0.73 (0.57–0.94) |
| Lidocaine | 0.49 (0.34–0.71) |
| Procaine | 2.3 (1.7–3.1) |

TABLE 3

Acute toxicity (mouse, i.v.) and Therapeutic Index

| COMPOUND | $LD_{50}$ mmols/kg/iv | Therapeutic Index $LD_{50}/ED_{50}$ |
| --- | --- | --- |
| Z. 1402 | 0.30 | 4 |
| Z. 1403 | 0.80 | 16 |
| Z. 1396 | 0.16 | 0.5 |
| Lidocaine | 0.14 | 0.28 |

The results, referred as dose which causes the death of the 50% of animals ($DL_{50}$), are shown in Table 3. In the same Table is also shown the Therapeutic Index which has been calculated as ratio between $DL_{50}$ and $ED_{50}$.

The above experimental data prove that the compounds of this invention show a remarkable local anesthetic activity also when compared with lidocaine and procaine which have been used as reference drugs.

As to their toxicity, they are less toxic than the reference drugs. Therefor, their therapeutic index is more favorable.

Finally, a further object of this invention are the pharmaceutical compositions containing, as active ingredient, the compounds of Formula I or their pharmaceutically acceptable salts together with organic or inorganic solid or liquid, pharmaceutical excipients.

The pharmaceutical dosage forms can be solid, such as tablets, dragées, capsules, powders, granules and suppositories, or liquid such as solutions, suspensions and emulsions, or semi-solids such as creams and ointments.

They can be also prepared in such a way to allow a substained release of the drug.

In addition they may contain preserving agents, stabilizers, wetting or emulsifying agents, salts for regulating the osmotic pressure, buffers, dyestuffs, flavouring agents etc. They may be prepared according to known methods and may further contain other therapeutic ingredients.

The following examples are given to illustrate this invention, without limiting it in any way.

EXAMPLE 1

(a) (1R,2R)-1-(4-methylthiophenyl-2-amino-1,3-propanediol (20 g; 98 mmols) is dissolved into a mixture of 1000 ml ethyl acetate and 600 ml of 0.5N of potassium hydroxyde under stirring at 5° C.

To the thus obtained solution are added in 1 hour and contemporaneously a solution of 3,3-diphenylpropionyl chloride (24 g; 98 mmols) in 220 ml of ethyl ether and 220 ml of 0.5N potassium hydroxide, while maintaining the pH at 7–8.

When the addition is over, precipitates a crystalline solid which, after 15 minutes at room temperature and under stirring, is collected by filtration (29.2 g).

The filtrate is washed twice with 0.5M sulfuric acid, then with 5% sodium bicarbonate aqueous solution and finally with water.

The organic extracts are dried over sodium sulfate and evaporated to dryness; 13 g.

The filtrate and the residue of the evaporation are combined and purified by dissolution in hot ethyl alcohol (450 ml), the solution is decoloured with active carbon and filtered; the filtrate is treated with water (380 ml) under stirring. After cooling, the precipitate is collected by filtration. (1R, 2R)-1-(4-methylthiophenyl)-2-(3,3-diphenylpropionylamino)-1,3-propanediol is thus obtained, 37.20 g; Yield, 90%; m.p. 168°–170° C.

In analogous manner has been prepared the enantiomer having 1S,2S configuration.

(b) A solution of (1S, 2S)-1-(4-methylthiophenyl)-2-(3,3-diphenylpropionylamino)-1,3-propanediol (15 g; 35.5 mmols) in anhydrous tetrahydrofuran (180 ml) is dropped into a suspension of lithium aluminium hydride (8 g; 210 mmols) in anhydrous tetrahydrofuran (360 ml) kept under vigorous stirring.

The thus obtained mixture is refluxed under stirring for about 45 hrs.

After cooling to 5° C., a 1:1 mixture (50 ml) of water and tetrahydrofuran is added under vigorous stirring.

The mixture is filtered through "theorite nr. 5" and the filtrate is evaporated to dryness.

The residue is extracted with ethyl ether and the extracts are washed with water and evaporated to dryness.

The oily residue (14.5 g) is dissolved in ethyl alcohol (70 ml). To the thus obtained solution is added maleic acid (4.5 g; 38.8 mmols) in ethyl alcohol (41 ml).

After cooling the precipitate (12.5 g) is filtered and purified by crystallization from water.

(1S, 2S)-1-(4-methylthiophenyl)-2-(3,3-diphenylpropylamino)-1,3-propanediol acid maleate; 8.4 g; Yield, 45%; m.p. 168°–170° C.

Analogously has been prepared the enantiomer having configuration (1R, 2R).

(c) (1R,2R)-1-(4-methylthiophenyl)-2-(3,3-diphenylpropylamino)-1,3-propanediol (4.08 g; 10 mmols) is added portionwise to acetic anhydride (8.15 ml) while keeping the temperature below 25° C.; the reaction mixture is then stirred for two hours.

The thus obtained solution is dropped into 8 ml of hydrogen peroxide (130 vol) while the temperature is maintained between 35° and 40° C.

When the addition is complete the reaction mixture is stirred for further 3,5 hours and then allowed to stand overnight at 4° C.

The solvent is removed by evaporation, ethyl ether (30 ml) and water (10 ml) are added to the residue, the ethereal extract is separated and evaporated to dryness.

The residue is refluxed with 13.5% hydrochloric acid (135 ml) for 1 hour and a half.

After cooling, the reaction mixture is extracted with ethyl ether. The aqueous layer is made alkaline and extracted many times with ethyl ether.

The organic extracts are combined and evaporated to dryness to afford a rough base (2.9 g) which is dissolved in methyl alcohol (13 ml) and added with a solution of maleic acid )(0.85 g) in ethyl alcohol (7 ml).

After cooling, filtration and drying, is obtained the (1R,2R)-1-(4-methylsulfonylphenyl)-2-(3,3-diphenylpropylamino)-1,3-propanediol maleate acid 3,35 g, Yield, 60%, m.p. 184°–186° C., which can be further purified by crystallization from water.

(d) In analogous manner has been prepared the enantiomer having configuration 1S, 2S.

EXAMPLE 2

A suspension of (1S,2S)-1-(4-methylsulfonylphenyl)-2-amino-1,3-propanediol (24.5 g; 0.1 mol) in toluene (200 ml), benzylacetone (15.5 g; 0.105 mol) and concentrate sulfuric acid (0.2 mol) is refluxed in a flask equipped with a Dean and Stark separator until are collected about 2 ml of water (about 16 hours).

After cooling and filtration, the solvent is removed by evaporation under reduced pressure.

The residue is dissolved in anhydrous tetrahydrofuran (200 ml) and dropped into a suspension of lithium aluminium hydride (11.4 g) in tetrahydrofuran (600 ml).

After two hours the excess of reducing agent is destroyed; the reaction mixture is filtered and the solvent is evaporated.

The residue is taken up with dichloromethane and washed with water. The evaporation of the organic phase leaves a crystalline product which is purified by crystallization from ethyl acetate.

It is thus obtained a diasteroisomer of (1S,2S)-1-(4-methylsulfonylphenyl-2-(1-methyl-3-phenyl-propylamino)-1,3-propanediol which melts at 120°–122° C.; 10.4 g.

Its hydrochloride salt is prepared in acetonitrile and purified from ethyl alcohol, m.p. 196°–198° C.

The mother liquors from which has been obtained the base by crystallization, contain the other stereoisomer which is converted into the corresponding hydrochloride in ethyl ether, m.p. 114°–116° C.

EXAMPLE 3

A suspension of (1S,2S)-1-(4-methylsulfonylphenyl)-2-amino-1,3-propanediol (49 g; 0.208 mol) in 80 ml of dichloromethane, 1,2dimethoxyethane (40 ml), phenoxyacetone (33 g; 0.22 mol) and concentrate sulfuric acid (0.5 ml) is refluxed in a flask equipped with a Dean and Stark separator until are collected about 3.6 ml of water (about 18 hours).

The reaction mixture is cooled and filtered, the solvent is removed by evaporation under reduced pressure.

The thick oily residue is dissolved in anhydrous tetrahydrofuran (500 ml) and dropped into a suspension of lithium aluminium hydride (22.8 g; 0.61 mol) in tetrahydrofuran (1070 ml) while keeping the temperature at room temperature.

After one hour and a half, the hydride in excess is destroyed and the reaction mixture is filtered through "Theorite nr 5". The filtrate is evaporated under reduced pressure and taken up with dichloromethane. The solution is worked up three times with 15% brine and then extracted many times with 5% hydrochloric acid. The aqueous extracts are washed with ethyl ether and then made alkaline with potassium carbonate. The oil which is formed is extracted with dichloromethane, the extracts are dried over sodium sulfate and evaporated under reduced pressure to afford a thick oil. This residue weights 71.9 g and is consisting of a mixture containing equal parts of the diasteroisomers of (1S,2S)-1-(4-methylsulfonylphenyl)-2-(1-methyl-2-phenoxyethylamino)-1,3-propanediol.

The separation of the two isomers is performed by chromatography through a silica gel column eluting with dichloromethane/methyl alcohol 95/5.

The products thus obtained crystallize from ethyl acetate/isopropyl ether 3/5. The one having the highest retention volume melts at 97°–99° C., the other melts at 90°–92° C.

In the same manner are prepared the enantiomers starting from the amine derivative having configuration 1R,2R.

Analogously to the methods disclosed in the foregoing examples it has been prepared the following product: R=CH$_3$; R1=H; R2=—CH$_2$—CH(CH$_3$)—C$_6$H$_5$; n=0 configuration: 1S,2S; m.p. 128°–130° C. (ethyl acetate).

We claim:
1. A compound of Formula

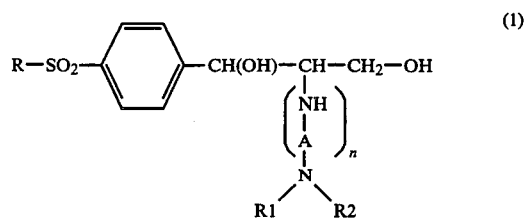

wherein
R is an alkyl group having from 1 to 4 carbon atoms;
n is 0 or 1;
A is an alkyl group having from 2 to 6 carbon atoms;
R1 is hydrogen or an alkyl group having from 1 to 6 carbon atoms;
R2 is an alkyl group having from 1 to 6 carbon atoms, a phenoxyalkyl group, a mono- or di-phenylalkyl radical where the alkyl group has from 1 to 6 carbon atoms and the phenyl moiety can be substituted by one or two substituents, equal or different between them, which are selected from the group consisting of halogen, 1–4 C alkyl and 1–4 C alkoxy, and pharmaceutically acceptable salts thereof with organic and inorganic pharmaceutically acceptable acids.

2. A compound according to claim 1, characterized in that
R is methyl or ethyl;
n is 0 or 1;
A is ethyl;
R1 is hydrogen, methyl or ethyl;
R2 is alkyl group having from 1 to 4 carbon atoms, phenoxyalkyl group, a mono- or a diphenylalkyl group where the alkyl group has 1–6 C and the phenyl moiety is substituted by one or two substituents, equal or different between them, which are selected from the group consisting of halogen and 1–4 C alkoxy.

3. Pharmaceutical composition comprising a Compound according to claim 1 together with one or more pharmaceutical excipients.

4. Pharmaceutical composition comprising a Compound according to claim 2 together with one or more pharmaceutical excipients.

5. A pharmaceutical composition suitable for use as an anesthetic comprising an amount of a compound according to claim 1 effective as a local anesthetic together with one or more pharmaceutical excipients.

6. A pharmaceutical composition suitable for use as an anesthetic comprising an amount of a compound according to claim 2 effective as a local anesthetic together with one or more pharmaceutical excipients.

7. A method of anesthetizing comprising administering an anesthetically effective amount of a compound of claim 1.

8. A method of anesthetizing comprising administering an anesthetically effective amount of a compound of claim 2.